United States Patent [19]

Waring

[11] 3,984,551
[45] Oct. 5, 1976

[54] PHARMACEUTICAL COMPOSITIONS COMPRISING PYRIDOQUINOLINE DERIVATIVES AND THE USE THEREOF

[75] Inventor: Wilson Shaw Waring, Macclesfield, England

[73] Assignee: Imperial Chemical Industries Limited, London, England

[22] Filed: Feb. 28, 1974

[21] Appl. No.: 447,056

Related U.S. Application Data

[60] Continuation-in-part of Ser. No. 399,341, Sept. 20, 1973, which is a division of Ser. No. 180,233, Sept. 13, 1971, Pat. No. 3,790,577.

[30] Foreign Application Priority Data

Apr. 16, 1973 United Kingdom............... 18188/73

[52] U.S. Cl............................... 424/248; 424/256; 424/258
[51] Int. Cl.$^2$............. A61K 31/535; A61K 31/435; A61K 31/47

[58] Field of Search..................... 424/248, 258, 256

[56] References Cited
UNITED STATES PATENTS

| | | | |
|---|---|---|---|
| 3,557,119 | 1/1971 | Hamber | 424/258 |
| 3,700,673 | 10/1972 | Watson | 424/258 |

*Primary Examiner*—Sam Rosen
*Attorney, Agent, or Firm*—Cushman, Darby & Cushman

[57] ABSTRACT

Pharmaceutical compositions comprising a 2,7-dicarboxy-4,9-dihydroxypyrido[2,3-g]quinoline derivative or a 2,8-dicarboxy-4,6-dihydroxypyrido[3,2-g]quinoline derivative. The compounds are active against syndromes or diseases initiated by an antigen-antibody reaction. Processes for the preparation of the compounds are also disclosed.

3 Claims, No Drawings

PHARMACEUTICAL COMPOSITIONS COMPRISING PYRIDOQUINOLINE DERIVATIVES AND THE USE THEREOF

This application is a continuation-in-part of U.S. application Ser. No. 399,341, filed Sept. 20, 1973, which itself was a divisional of U.S. application Ser. No. 180,233, filed Sept. 13, 1971 (now U.S. Pat. No. 3,790,577).

This invention relates to heterocyclic compounds, and more particularly it relates to new pyridoquinoline derivatives which are active as inhibitors of the effects following the combination of reagin-like antibodies and their antigens. They are therefore useful for the treatment of asthma, for example allergic asthma, and they may also be useful for the treatment of other syndromes or diseases initiated by an antigen-antibody reaction, for example hay fever, urticaria and auto-immune diseases.

According to the invention there are provided pyridoquinoline derivatives of the formula:

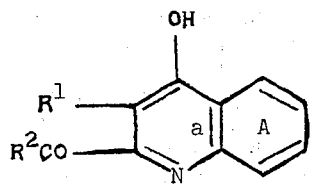

wherein benzene ring A stands for a group of the formula:

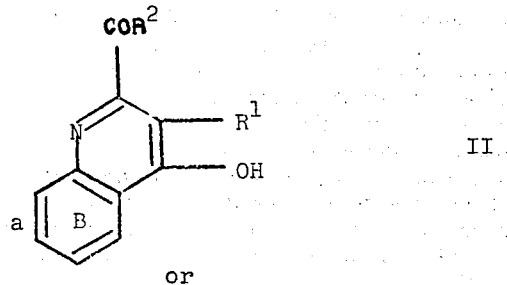

or

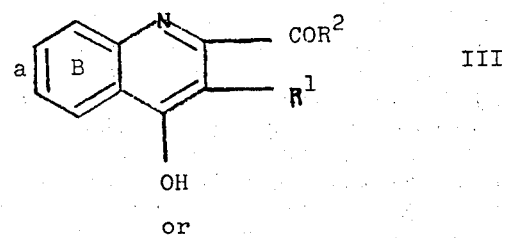

or

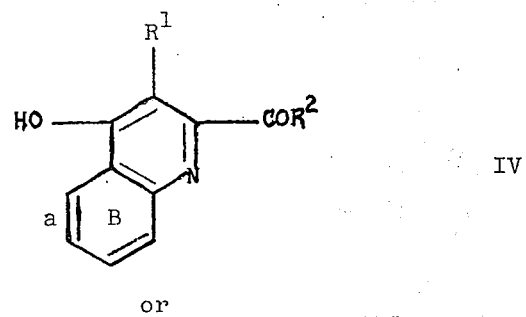

or

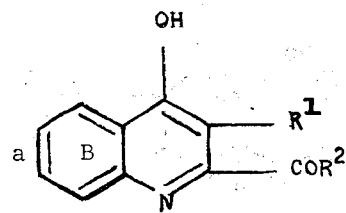

wherein $a$ in formulae II to V indicates the common bond between the pyridine ring and the benzene ring A in formula I; $R^1$ stands for hydrogen or a methyl radical; $R^2$ stands for a hydroxy, $C_{1-6}$ alkoxy, $C_{7-10}$ phenylalkoxy or phenoxy radical; and the benzene ring B may optionally bear not more than two substituents selected from $C_{1-8}$ alkyl, cycloalkyl of not more than 6 carbon atoms, $C_{1-6}$ alkoxy, trifluoromethyl, phenyl and phenoxy radicals, and halogen atoms, and $NR^3R^4$ radicals wherein $R^3$ stands for a $C_{1-6}$ alkyl radical and $R^4$ stands for a $C_{1-6}$ alkyl or phenyl radical or wherein $-NR^3R^4$ stands for a nitrogen-containing heterocyclic radical of not more than 7 ring atoms; or, in the case of formula II or IV, the said benzene ring B may optionally bear an alkylene radical of 3–5 carbon atoms; and wherein when $R^1$ stands for a methyl radical, the compounds are 1,7-phenanthroline derivatives only, bearing either a $C_{1-5}$-alkyl $C_{1-4}$-alkoxy, phenoxy, piperidino or morpholino substituent in the 5- or 6-position, or 5,6-dimethyl or 5-phenyl-6-methoxy substituents, or a 5,6-alkylene substituent of 3–5 carbon atoms; and non-toxic pharmaceutically-acceptable salts thereof; but excluding 2,8-dicarboxy-4,10-dihydroxy-1,7-phenanthroline and di-$C_{1-6}$-alkyl esters thereof, and 4,9-dihydroxy-2,7-dimethoxycarbonylpyrido[2,3-g]quinoline, and non-toxic pharmaceutically-acceptable salts thereof.

It will be understood by those skilled in the art that the pyridoquinoline derivatives of the invention consist of compounds having the following formulae:

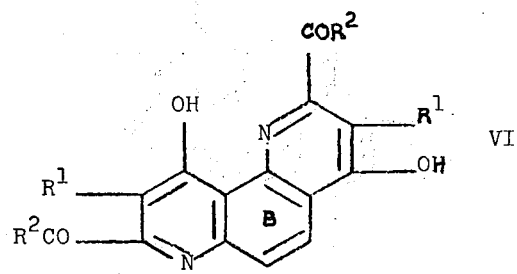

(1,7-phenanthroline derivatives)

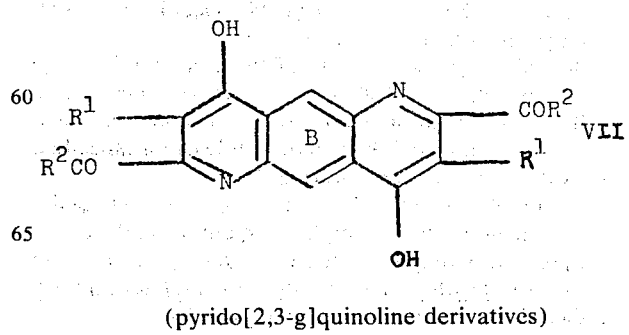

(pyrido[2,3-g]quinoline derivatives)

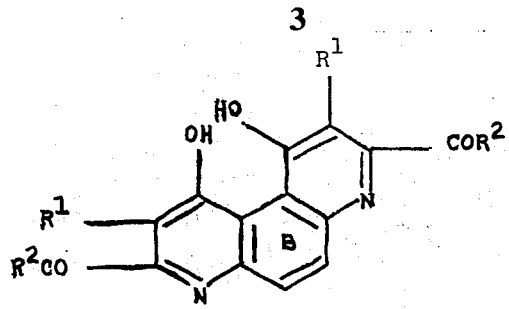

(4,7-phenanthroline derivatives)

and

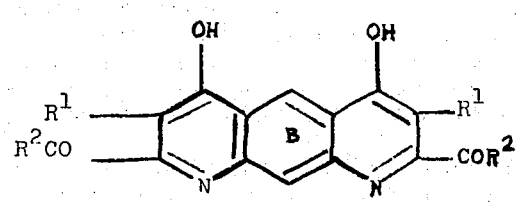

(pyrido[3,2-g]quinoline derivatives)

wherein B, $R^1$ and $R^2$ have the meanings stated above, and non-toxic pharmaceutically-acceptable salts thereof, but excluding the compounds specified above.

It is to be understood that the compounds of the invention can exist in a tautomeric quinolone form, for example, in the case of the compounds of formula VI, the tautomeric form having the formula:

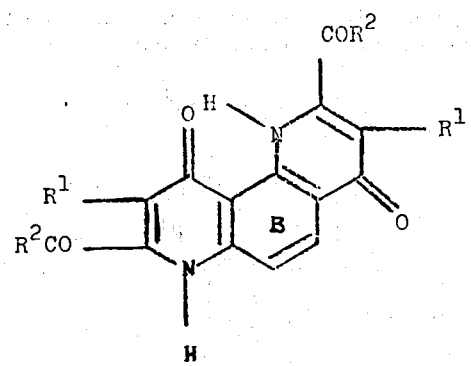

However, for convenience the compounds of the invention will all be referred to in this specification as 4-hydroxyquinoline derivatives.

As indicated above, those of the compounds of the invention wherein $R^1$ stands for a methyl radical are all 1,7-phenanthroline derivatives (i.e. formulae I, II and VI are relevant) and they all bear at least one specified substituent in the benzene ring B.

A suitable value for $R^2$ when it stands for a $C_{1-6}$ alkoxy radical is, for example, a methoxy, ethoxy, n-propoxy, n-butoxy or n-pentyloxy radical. A suitable value for $R^2$ when it stands for a $C_{7-10}$ phenylalkoxy radical is, for example, a benzyloxy radical.

Ring B may optionally bear not more than two substituents selected from, for example, methyl, ethyl, propyl, butyl, pentyl, hexyl, heptyl, octyl, cyclohexyl, methoxy, ethoxy, propoxy, trifluoromethyl, phenyl, phenoxy, dimethylamino, diethylamino, dipropylamino, dibutylamino and N-methylanilino radicals, and saturated heterocyclic radicals of 5,6 or 7 ring atoms, containing a nitrogen atom as hetero-atom and optionally containing a second hetero-atom which is an oxygen atom, for example a piperidino, 1-hexahydroazepinyl or morpholino radical, and fluorine, chlorine and bromine atoms. Alternatively, in the case of compounds of the formula VI or VIII, ring B may optionally bear, for example, a trimethylene, tetramethylene or pentamethylene radical.

As stated above, when $R^1$ stands for a methyl radical, ring B always bears one or two specified substituent(s), and suitable substituents are mentioned immediately above.

Compounds of the invention which are preferred because of their high activity are 1,7-phenanthroline derivatives (i.e. formulae I, II and VI are relevant) wherein $R^1$ stands for hydrogen, $R^2$ stands for a hydroxy radical, and the benzene ring B bears a $C_{3-5}$ alkyl radical in the 6-position of the nucleus, for example an n-propyl, n-butyl, t-butyl or n-pentyl radical, and in particular and n-propyl or n-butyl radical, and non-toxic pharmaceutically-acceptable salts thereof.

Suitable salts of the invention in the case where the said compounds of formula I are sufficiently basic are acid-addition salts derived from inorganic or organic acids affording non-toxic pharmaceutically-acceptable anions, for example hydrochlorides, hydrobromides, tartrates or citrates. Suitable salts of the invention in the case where the said compounds of formula I are sufficiently acidic, i.e. wherein $R^2$ stands for a hydroxy radical and/or wherein the ring hydroxy radical(s) is or are sufficiently acidic, are salts containing a non-toxic pharmaceutically-acceptable cationic moiety; for example, ammonium, alkali metal, alkaline earth metal or aluminum salts, or salts with non-toxic pharmaceutically-acceptable organic bases, for example morpholine, N-methylglucamine, piperidine, triethanolamine or ethylenediamine.

Particularly preferred compounds of the invention are 6-n-butyl-2,8-dicarboxy-4,10-dihydroxy-1,7-phenanthroline, 2,8-dicarboxy-4,10-dihydroxy-6-n-propyl-1,7-phenanthroline and 2,8-dicarboxy-4,10-dihydroxy-6-n-pentyl-1,7-phenanthroline, and non-toxic pharmaceutically-acceptable salts thereof.

According to a further feature of the invention there is provided a process for the manufacture of those of the compounds of the formula I wherein A and $R^1$ have the meanings stated above and $R^2$ stands for a $C_{1-6}$ alkoxy radical, and non-toxic pharmaceutically-acceptable salts thereof, which comprises reacting a diamino compound of the formula:

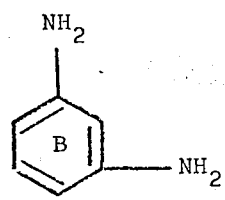

or

XII wherein B has the meaning stated above, with a compound of the formula:

$$R^2CO.CHR^1.CO.COR^2 \qquad XIII$$

wherein $R^1$ and $R^2$ have the meanings stated immediately above (i.e. the Conrad-Limpach reaction).

The Conrad-Limpach reaction involves two stages. In the first stage a compound is produced which is one of its tautomeric forms has one of the formulae:

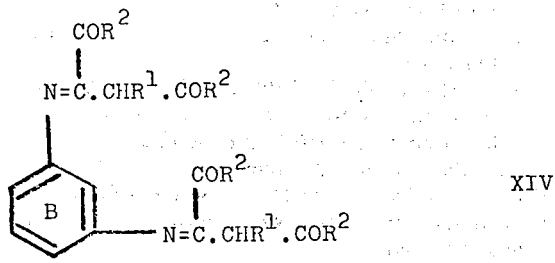

XIV and

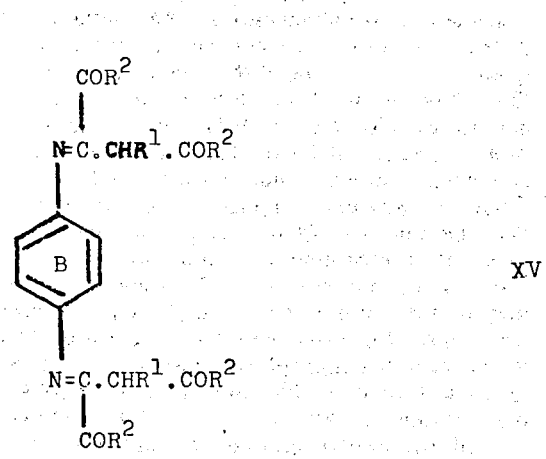

XV wherein B, $R^1$ and $R^2$ have the meanings stated immediately above, depending upon which of the said diamino compounds is used as starting material. This stage is carried out at a moderately elevated temperature, for example 80°–110°C., in an aromatic hydrocarbon solvent, for example benzene, in an apparatus which facilitates the removal of water (formed during the reaction) from the reaction mixture, for example a Dean and Stark apparatus.

The second stage of the Conrad-Limpach reaction involves ring-closing the compound of formula XIV or XV so as to obtain a compound of formula VI, VII, VIII or IX, wherein B, $R^1$ and $R^2$ have the meanings stated immediately above. This stage may be carried out by heating the compound of formula XIV or XV at 230°–250°C., for example by heating it in diphenyl ether or α-chloronaphthalene at 230°–250°C., or by reacting the compound of formula XIV or XV with polyphosphoric acid at 130°–180°C., for example 150°C. It is to be understood that ring-closure of the compound of formula XIV gives products of formulae VI and IX, and ring-closure of the compound of formula XV gives products of formulae VII and VIII.

According to a further feature of the invention there is provided a process for the manufacture of those of the compounds of formula I wherein A has the meaning stated above, $R^1$ stands for hydrogen, and $R^2$ stands for a $C_{1-6}$ alkoxy, $C_{7-10}$ phenylalkoxy or phenoxy radical, and non-toxic pharmaceutically-acceptable salts thereof, which comprises reacting a diamino compound of the formula XI or XII with an acetylene derivative of the formula:

$$R^2CO.C \equiv C.COR^2 \qquad XVI$$

wherein $R^2$ has the meaning stated immediately above, so as to give a compound which in one of its tautomeric forms has the formula XIV or XV, respectively, wherein $R^1$ stands for hydrogen, and then ring-closing this compound, for example by either of the methods described above, to give the desired product.

According to a further feature of the invention there is provided a proces for the manufacture of those of the compounds of formula I wherein A and $R^1$ have the meanings stated above and $R^2$ stands for a hydroxy radical, which comprises hydrolysing the corresponding alkyl, phenylalkyl or phenyl ester or the corresponding nitrile or amide.

The hydrolysis is carried out in the presence of water, and an organic solvent may optionally be present. As a suitable hydrolytic agent there may be mentioned, for example, an alkali metal hydroxide, for example sodium or potassium hydroxide, or an inorganic acid, for example hydrochloric acid, optionally in the presence of acetic acid.

According to a further feature of the invention there is provided a process for the manufacture of those of the compounds of the formula I wherein A and $R^1$ have the meanings stated above and $R^2$ stands for a $C_{1-6}$ alkoxy radical, which comprises esterifying the appropriate carboxylic acid, i.e. wherein $R^2$ stands for a hydroxy radical, or trans-esterifying an appropriate ester.

General methods of esterification of carboxylic acids, and of trans-esterification, are well known in the chemical art. Thus, for example, the appropriate carboxylic acid may be esterified by reacting it with the appropriate hydroxy compound of the formula $R^2H$, wherein $R^2$ stands for a $C_{1-6}$ alkoxy radical, and a suitable acid, for example an inorganic acid, for example hydrochloric acid. The reaction may conveniently be carried out at a moderately elevated temperature, for example at reflux temperature. Alternatively, for example, an acid halide or anhydride of the said carboxylic acid may be reacted with the said hydroxy compound, optionally in the presence of an organic solvent.

The salts of the invention, and the compounds used as starting materials in the processes of the invention, are all obtainable by means of well known general processes, as indicated in the Examples.

The compounds of the invention, and the pharmaceutcial compositions of the invention which are described hereinafter, exhibit the above-mentioned activity when administered by inhalation or intravenously. Furthermore, some of the esters of the invention, and some of the esters which are active ingredients of the pharmaceutical compositions of the invention, are orally active also. In particular, diethyl esters are orally active.

The activity of the compounds and pharmaceutical compositions of this invention is demonstrated by their ability to inhibit, in the rat, passive cutaneous anaphylaxis induced by reaginic antibodies to egg albumin, using *B. pertussis* as an adjuvant. When the said compounds are used to treat asthma in man by inhalation, a typical dose is from 0.01mg./kg. to 1mg./kg. at suitable intervals, for example at 6-hourly intervals during the day. When they are used intravenously to treat asthma in man, a typical total daily dose is 25mg. per man. When the appropriate compounds which are esters are used orally to treat asthma in man, a typical dose is 50 to 200mg. per man, three times a day. When the said compounds are used to treat other syndromes or diseases initiated by an antigen-antibody reaction, a typical total daily dose is 1 to 50mg. per man when given by inhalation, 25mg. per man when given intravenously, and 300mg. per man when given orally.

According to a further feature of the invention there are provided pharmaceutical compositions comprising a compound of the formula I, wherein the benzene ring A stands for a group of the formula II, III, IV or V, wherein in a formulae II to V indicates the common bond between the pyridine ring and the benzene ring A in formula I; $R^1$ stands for hydrogen or a methyl radical; $R^2$ stands for a hydroxy, $C_{1-6}$ alkoxy, $C_{7-10}$ phenylalkoxy or phenoxy radical; and the benzene ring B may optionally bear not more than two substituents selected from $C_{1-8}$ alkyl, cycloalkyl of not more than 6 carbon atoms, $C_{1-6}$ alkoxy, trifluoromethyl, phenyl and phenoxy radicals, and halogen atoms, and $NR^3R^4$ radicals wherein $R^3$ stands for a $C_{1-6}$ alkyl radical and $R^4$ stands for a $C_{1-6}$ alkyl or phenyl radical or wherein $—NR^3R^4$ stands for a nitrogen-containing heterocyclic radical of not more than 7 ring atoms or, in the case of formula II or IV, the said benzene ring B may optionally bear an alkylene radical of 3–5 carbon atoms; and wherein when $R^1$ stands for a methyl radical, the compounds are 1,7-phenanthroline derivatives only, bearing either a $C_{1-5}$-alkyl, $C_{1-4}$-alkoxy, phenoxy, piperidino or morpholino substituent in the 5- or 6-position, or 5,6-dimethyl or 5-phenyl-6-methoxy substituents, or a 5,6-alkylene substituent of 3–5 carbon atoms; or a non-toxic pharmaceuticaly-acceptable salt thereof; and an inert non-toxic pharmaceutically-acceptable diluent or carrier.

The pharmaceutical compositions of the invention are obtainable by well known methods using conventional diluents or carriers.

Suitable compositions for administration by inhalation comprise a mixture of the active ingredient with a solid diluent or carrier, for example lactose, the said mixture being in fine particulate form suitable for administration from a powder inhalation device. Alternatively, the compositions may be administered by inhalation in the form of a suspension or solution in a suitable liquid, for example water or an aqueous or non-aqueous medium, using a conventional nebulizer or a pressurised container.

Alternatively, the said compositions may be in a form suitable for intravenous administration, for example sterile aqueous solutions.

Alternatively, the said compositions may be orally-administrable compositions, for example an orally-administrable unit dosage form, for example a tablet or capsule, or a solution, suspension, emulsion or syrup.

The pharmaceutical compositions of the invention may contain, in addition to a compound of the formula I, or a non-toxic pharmaceutically-acceptable salt thereof, one or more other known active ingredients selected from β-adrenergic stimulants, for example isoprenaline, adrenaline, orciprenaline or isoethacine, or a pharmaceutically acceptable acid addition salt thereof, for example a sulphate, and prostaglandins having bronchodilatory activity, for example prostaglandin $E_1$ and $E_2$, and phosphodiesterase inhibitors selected from the following compounds:

a. 3-acetamido-6-methyl-8-n-propyl-s-triazolo[4,3-a]pyrazine;

b. 2-amino-4,6-di-$C_{1-4}$-alkyl-5-oxo-4,5-dihydro-s-triazolo[1,5-a]pyrimidines, for example 2-amino-6-methyl-5-oxo-4-n-propyl-4,5-dihydro-s-triazolo[1,5-a]pyrimidine;

c. theophylline and related 3,5-di-$C_{1-4}$-alkylxanthines; and d. 6,8-di-$C_{1-4}$-alkyl-5,6-dihydro-5-oxo-s-triazolo[4,3-c]pyrimidines, for example 5,6-dihydro-5-oxo-6,8-di-n-propyl-s-triazolo[4,3-c]pyrimidine.

The pharmaceutical compositions of the invention may contain from 1% to 50% by weight of a compound of formula I or a non-toxic pharmaceutically acceptable salt thereof.

The invention is illustrated but not limited by the following Examples.

EXAMPLE 1

Sodio diethyl oxalacetate (15.8g.) was added portionwise to a stirred mixture of 10N-hydrochloric acid (10ml.), water (100ml.) and benzene (50ml.) at a temperature not exceeding 20°C. The mixture was stirred for 1 hour and the benzene layer was then separated and washed with water (50ml.). The aqueous washings were back-extracted with benzene (50ml.) and the combined benzene solutions were dried over anhydrous magnesium sulphate and filtered. 2,4-Diaminotoluene (3.2g.) was added and the mixture was boiled in an apparatus for continuously removing water from the reaction mixture (a Dean and Stark apparatus) until no more water was collected. The benzene was removed in vacuo and the residue was added over 5 minutes to boiling diphenyl ether (100ml.). The mixture was heated at 220°–240°C. until no more ethanol was liberated (about 5 minutes). The solution was cooled to room temperature and diluted by the addition of petroleum ether (b.p. 40°–60°C.; 500ml.). After standing for 30 minutes, the suspension was filtered and the solid residue washed several times with acetone. There was thus obtained, as solid residue, 2,8-diethoxycarbonyl-4,10-dihydroxy-6-methyl-1,7-phenanthroline, m.p. 198°–200°C.

EXAMPLE 2

2,8-Diethoxycarbonyl-4,10-dihydroxy-6-methyl-1,7-phenanthroline (1g.) was heated with 10% w/v aqueous sodium hydroxide (10ml.) on a steam bath for 30 minutes. The mixture was cooled, filtered, and the solid residue of sodium salt was dissolved in water (10ml.). The solution was acidified with concentrated hydrochloric acid. The resultant precipitate was collected by filtration, dissolved in saturated sodium hydrogen carbonate solution (15ml.), filtered, and the filtrate acidified with concentrated hydrochloric acid. The resultant precipitate was collected by filtration, and washed successively with water and hot ethanol. There was thus obtained 2,8-dicarboxy-4,10-dihydroxy-6-methyl-1,7-phenanthroline, m.p. 316°C. (decomposition).

EXAMPLE 3

The methods described in Examples 1 and 2 were repeated using the appropriate phenylenediamine as starting material, and the following compounds were obtained:

2,8-dicarboxy-4,10-dihydroxy-5,6-dimethyl-1,7-phenanthroline, m.p. 310°–314°C. (decomposition), from 1,3-diamino-4,5-dimethylbenzene;

3,8-dicarboxy-1,10-dihydroxy-5,6-dimethyl-4,7-phenanthroline, m.p. 306°C. (crystallised from dimethylsulphoxide), from 1,4-diamino-2,3-dimethylbenzene;

3,8-dicarboxy-1,10-dihydroxy-4,7-phenanthroline, m.p. 306°–308°C., from p-phenylenediamine; and 2,7-dicarboxy-4,9-dihydroxy-5,10-dimethylpyrido[2,3-g]quinoline, m.p. over 350°C., from 1,4-diamino-2,5-dimethylbenzene.

It should be noted that the structure of the next-to-last product named above, i.e. the supposed 4,7-phenanthroline derivative of m.p. 306°–308°C., is not known with complete certainty. It is believed that the product was as it has been named; however, in fact it may have been 2,7-dicarboxy-4,9-dihydroxypyrido[2,3-g]quinoline.

EXAMPLE 4

The methods described in Examples 1 and 2, as appropriate, were repeated using the appropriate phenylenediamine as starting material, and the following compounds were obtained:

2,8-diethoxycarbonyl-6-ethyl-4,10-dihydroxy-1,7-phenanthroline, m.p. 183°–184°C. (crystallised from ethyl acetate), and 2,8-dicarboxy-6-ethyl-4,10-dihydroxy-1,7-phenanthroline, m.p. 310°C. (decomposition), from 2,4-diamino-1-ethylbenzene;

6-t-butyl-2,8-diethoxycarbonyl-4,10-dihydroxy-1,7-phenanthroline, m.p. 253°–254°C. (crystallised from ethanol), and 6-t-butyl-2,8-dicarboxy-4,10-dihydroxy-1,7-phenanthroline, m.p. 315°C. (decomposition), from 2,4-diamino-1-t-butylbenzene;

2,8-dicarboxy-4,10-dihydroxy-6-isopropyl-1,7-phenanthroline, m.p. 306°–307°C. (decomposition), from 2,4-diamino-1-isopropylbenzene; and 6-chloro-2,8-diethoxycarbonyl-4,10-dihydroxy-1,7-phenanthroline, m.p. 155°–157°C., and 6-chloro-2,8-dicarboxy-4,10-dihydroxy-1,7-phenanthroline, m.p. over 300°C., from 1,3-diamino-4-chlorobenzene.

EXAMPLE 5

3,8-Dimethoxycarbonyl-1,10-dihydroxy-5-methyl-4,7-phenanthroline was hydrolysed by the process described in Example 2, and there was thus obtained 3,8-dicarboxy-1,10-dihydroxy-5-methyl-4,7-phenanthroline, m.p. 295°C. (decomposition), (crystallised from 75% v/v dimethylsulphoxide/ethanol).

The 3,8-dimethoxycarbonyl-1,10-dihydroxy-5-methyl-4,7-phenanthroline used as starting material was obtained as follows:

Sodium hydride (2.4g. of a 50% suspension in mineral oil) was added gradually to a stirred, cooled suspension of 2,5-diaminotoluene dihydrochloride in dry methanol (100ml.), keeping the temperature between 10° and 15°C. The solution was allowed to rise to room temperature, and then dimethyl acetylenedicarboxylate (7.1g.) in dry methanol (10ml.) was added. After the resulting exothermic reaction had finished, the mixture was heated under reflux for 3 hours, and then filtered, and the filtrate was evaporated under reduced pressure. The residue solidified on trituration with ether, and was crystallised from methanol to give the bis anil, m.p. 90°–92°C.

The bis anil was added to boiling diphenyl ether (100ml.), and the mixture was maintained at 220°–240°C. until no more methanol was liberated (about 5 minutes). The solution was cooled, and the resulting yellow solid filtered off, and washed with petroleum ether (b.p. 40°–60°C.), and then crystallised from pyridine. There was thus obtained 3,8-dimethoxycarbonyl-1,10-dihydroxy-5-methyl-4,7-phenanthroline, m.p. 302°–304°C.

EXAMPLE 6

2,8-Dicarboxy-4,10-dihydroxy-6-methyl-1,7-phenanthroline (0.8g.) was stirred with a solution of sodium hydrogen carbonate (0.3g.) in water (5ml.) for one hour. The mixture was filtered, the filtrate was diluted with ethanol (12ml.), and the resulting mixture was filtered. The solid residue was successively washed with hot ethanol and ether, and then dried. There was thus obtained the disodium salt of 2,8-dicarboxy-4,10-dihydroxy-6-methyl-1,7-phenanthroline, as a dihydrate; n.m.r. spectrum (in $D_2O$): —$CH_3$ single peak (2.1 $\delta$); $H_3$, $H_9$ single peak for two protons (6.4 $\delta$); $H_5$ single peak (7.15 $\delta$).

EXAMPLE 7

A solution of acetylene dicarboxylic acid dimethyl ester (8.4g.) in dry methanol (50ml.) was added to a solution of 2,4-diamino-1-n-butylbenzene (6g.) in dry methanol (50ml.) and, when the exothermic reaction was over, the mixture was heated under reflux for 3 hours. The methanol was removed by distillation under reduced pressure, the residue was dissolved in ether (200ml.), and washed successively with water (2 × 100ml.), N-hydrochloric acid (2 × 100ml.), N-sodium hydroxide (2 × 200ml.) and water (2 × 100ml.). The ethereal solution was dried over anhydrous magnesium sulphate, filtered, and the solvent was removed by distillation. The residual oil was added to boiling diphenyl ether (100ml.), and the mixture was kept at 220°–240°C. until no more methanol was liberated (about 5 minutes). The solution was cooled and diluted with petroleum ether (b.p. 40°–60°C.; 500ml.). After standing for 30 minutes, the petroleum ether was decanted from the precipitated oil, and the oil was rubbed in the presence of acetone. The resultant mixture was filtered, and the solid residue (m.p. 170°–175°C.) was crystallised from 2-ethoxyethanol and then washed with ether. There was thus obtained 6-n-butyl-2,8-dimethoxycarbonyl-4,10-dihydroxy-1,7-phenanthroline, m.p. 175°–177°C.

The 2,4-diamino-1-n-butylbenzene used as starting material was obtained as follows:

n-Butylbenzene (25g.) was added gradually over a period of 1 hour to a stirred mixture of concentrated sulphuric acid (122ml.) and concentrated nitric acid (66ml.; density 1.42) heated at 40°C. When the addition was complete, the mixture was heated at 40°C. for 45 minutes and then at 100°C. for 45 minutes. The mixture was cooled, poured on to ice, and the resulting oil was extracted twice with ether (200ml.). The ethereal solution was washed successively with water, sodium carbonate solution and water. The ethereal solution was dried over anhydrous magnesium sulphate, filtered, and the solvent was removed by distillation. The residue was fractionally distilled under reduced pressure and a fraction collected at b.p. 140°–144°C./1mm. There was thus obtained 1-n-butyl-2,4-dinitrobenzene.

A solution of 1-n-butyl-2,4-dinitrobenzene (10g.) in ethanol (100ml.) was shaken with hydrogen at room temperature and atmospheric pressure in the presence of palladium-on-charcoal (0.5g. of 5%) as catalyst. When the theoretical amount of hydrogen (5.2 l.) had been absorbed, the mixture was filtered and the filtrate evaporated to dryness under reduced pressure. The residue of 2,4-diamino-1-n-butylbenzene (diacetyl derivative, m.p. 209°–210°C., crystallised from ethanol) was used directly for the subsequent reaction with acetylene dicarboxylic acid dimethyl ester.

EXAMPLE 8

6-n-Butyl-2,8-dimethoxycarbonyl-4,10-dihydroxy-1,7-phenanthroline (1g.) was heated with 10% w/v aqueous sodium hydroxide (10ml.) on a steam bath for 30 minutes. The hot solution was acidified with concentrated hydrochloric acid and the resultant precipitate was collected by filtration, dissolved in saturated sodium hydrogen carbonate solution (15ml.), filtered, and the filtrate acidified with concentrated hydrochloric acid. The resultant precipitate was collected by filtration, washed successively with water and ethanol, crystallised from dimethylsulphoxide, and washed with hot ethanol. There was thus obtained 6-n-butyl-2,8-dicarboxy-4,10-dihydroxy-1,7-phenanthroline, m.p. 300°C. (decomposition).

EXAMPLE 9

The methods described in Examples 7 and 8 were repeated using the appropriate phenylenediamine as starting material, and the following compounds were obtained:

6-s-butyl-2,8-dicarboxy-4,10-dihydroxy-1,7-phenanthroline, m.p. 308°C. (decomposition) (crystallised from dimethylsulphoxide) from 2,4-diamino-1-s-butylbenzene;

2,8-dicarboxy-6-cyclohexyl-4,10-dihydroxy-1,7-phenanthroline, m.p. 314°C. (decomposition) (crystallised from dimethylsulphoxide) from 2,4-diamino-1-cyclohexylbenzene;

2,6-dicarboxy-4,8-dihydroxy-9,10,11,12-tetrahydrobenzo[f][1,7]phenanthroline, m.p. 318°–320°C. (decomposition) (crystallised from dimethylsulphoxide and washed with ethanol) from 5,7-diamino-1,2,3,4-tetrahydronaphthalene;

2,8-dicarboxy-4,10-dihydroxy-6-n-pentyl-1,7-phenanthroline, m.p. 297°–300°C. (decomposition) (crystallised from dimethylsulphoxide) from 2,4-diamino-1-n-pentylbenzene;

2,8-dicarboxy-6-n-hexyl-4,10-dihydroxy-1,7-phenanthroline, m.p. 294°C. (decomposition) (crystallised from dimethylsulphoxide) from 2,4-diamino-1-n-hexylbenzene;

2,8-dicarboxy-4,10-dihydroxy-6-n-octyl-1,7-phenanthroline, m.p. 300°C. (decomposition) (crystallised from dimethylsulphoxide and washed with ethanol) from 2,4-diamino-1-n-octylbenzene; and 2,8-dicarboxy-4,10-dihydroxy-6-methoxy-5-phenyl-1,7-phenanthroline, m.p. 277°–278°C. (decomposition) from 3,5-diamino-2-methoxydiphenyl.

The 2,4-diamino-1-n-pentylbenzene used in the preparation of the said 6-n-pentyl derivative was obtained by hydrogenation of 2,4-dinitro-1-n-pentylbenzene in a similar way to that described in Example 7 for the hydrogenation of 1-n-butyl-2,4-dinitrobenzene. The 2,4-diamino-1-n-pentylbenzene so obtained (diacetyl derivative, m.p. 200°–202°C., crystallised from aqueous methanol) was used directly for the reaction with acetylene dicarboxylic acid dimethyl ester.

The said 2,4-dinitro-1-n-pentylbenzene was obtained as follows:

Fuming nitric acid (40ml., d 1.5) was added gradually to n-pentylbenzene with stirring and cooling so that the temperature remained below 5°C. When the addition was complete, the mixture was stirred at 30°C. for 90 minutes, then poured into ice-water and the resulting oil extracted with ether. The ethereal extract was washed successively with water, sodium carbonate solution and water. The ethereal solution was dried over anhydrous magnesium sulphate, filtered, and the solvent was removed by distillation. The residue (29g.) was stirred vigorously while fuming nitric acid (90ml., d 1.5) was added slowly, allowing the temperature to rise to 60°C. without external cooling. When the addition was complete the mixture was stirred and heated at 45°–50°C. for 2 hours. The mixture was poured into ice-water, the oil extracted with ether, and the ethereal extract washed successively with water, sodium carbonate solution, and water. The ethereal solution was dried over anhydrous magnesium sulphate, filtered, and the solvent removed by distillation. The residual oil was fractionally distilled under reduced pressure, and there was thus obtained 2,4-dinitro-1-n-pentylbenzene, b.p. 150°–156°C./0.7mm.

The 2,4-diamino-1-n-hexylbenzene used in the preparation of the said 6-n-hexyl derivative was obtained by hydrogenation of 1-n-hexyl-2,4-dinitrobenzene in a similar way to that described in Example 7 for the hydrogenation of 1-n-butyl-2,4-dinitrobenzene. The 2,4-diamino-1-n-hexylbenzene so obtained (diacetyl derivative, m.p. 198°–199°C., crystallised from aqueous methanol) was used directly for the reaction with acetylene dicarboxylic acid dimethyl ester. The said 1-n-hexyl-2,4-dinitrobenzene was obtained by nitration of n-hexylbenzene in a similar manner to that described above for the nitration of n-pentylbenzene.

The 2,4-diamino-1-n-octylbenzene used in the preparation of the said 6-n-octyl derivative was obtained by hydrogenation of 2,4-dinitro-1-n-octylbenzene in a similar way to that described in Example 7 for the hydrogenation of 1-n-butyl-2,4-dinitrobenzene. The 2,4-diamino-1-n-octylbenzene so obtained (diacetyl derivative, m.p. 195°–197°C., crystallised from methanol) was used directly for the reaction with acetylene dicarboxylic acid dimethyl ester.

The 3,5-diamino-2-methoxydiphenyl used in the preparation of the said 6-methoxy-5-phenyl derivative was obtained by hydrogenation of 2-methoxy-3,5-dinitrodiphenyl (as a suspension in ethanol) in a similar way to that described in Example 7 for the hydrogenation of 1-n-butyl-2,4-dinitrobenzene. The 3,5-diamino-2-methoxydiphenyl so obtained (diacetyl derivative, m.p. 169°–170°C., crystallised from methyl acetate) was used directly for the reaction with acetylene dicarboxylic acid dimethyl ester.

EXAMPLE 10

The method described in Example 1 was repeated using an equivalent amount of the appropriate phenylenediamine as starting material, and the following compounds were obtained:

2,8-diethoxycarbonyl-4,10-dihydroxy-6-n-propyl-1,7-phenanthroline, m.p. 212°–214°C. (crystallised from ethanol or 2-ethoxyethanol), from 2,4-diamino-1-n-propylbenzene; and 6-n-butyl-2,8-diethoxycarbonyl-4,10-dihydroxy-1,7-phenanthroline, m.p. 192°–193°C. (crystallised from ethanol), from 2,4-diamino-1-n-butylbenzene.

The 2,4-diamino-1-n-propylbenzene used as starting material was obtained as follows:

A solution of 2,4-dinitro-1-n-propylbenzene (10g.) in ethanol (125ml.) was shaken with hydrogen at room temperature and atmospheric pressure in the presence of palladium-on-charcoal (0.5g. of 5%) as catalyst. When the theoretical amount of hydrogen (6.4 l.) had been absorbed, the mixture was filtered and the filtrate evaporated to dryness under reduced pressure. The residue of 2,4-diamino-1-n-propylbenzene was used directly for the reaction with diethyl oxalacetate.

EXAMPLE 11

2,8-Diethoxycarbonyl-4,10-dihydroxy-6-n-propyl-1,7-phenanthroline was hydrolysed with hot aqueous sodium hydroxide by the method described in Example 8, and there was thus obtained 2,8-dicarboxy-4,10-dihydroxy-6-n-propyl-1,7-phenanthroline, m.p. 306°C. (decomposition) (crystallised from dimethylsulphoxide, and washed with ethanol).

EXAMPLE 12

2,8-Dimethoxycarbonyl-4,6-dihydroxy-10-methylpyrido[3,2-g]quinoline was hydrolysed with hot aqueous sodium hydroxide by the method described in Example 8. There was thus obtained 2,8-dicarboxy-4,6-dihydroxy-10-methylpyrido[3,2-g]quinoline, m.p. above 300°C., (crystallised from dimethylsulphoxide).

The 2,8-dimethoxycarbonyl-4,6-dihydroxy-10-methylpyrido[3,2-g]quinoline used as starting material was obtained as follows:

A solution of acetylene dicarboxylic acid dimethyl ester (2.8g.) in dry methanol (20ml.) was added to a solution of 2,6-diamino-1-methylbenzene (1.2g.) in dry methanol (20ml.), and the mixture heated under reflux for 3 hours. The mixture was then cooled and filtered, and the solid residue of bis anil (1.9g., m.p. 194°–196°C., crystallised from dimethylformamide) was added in portions to boiling diphenyl ether (50ml.), and the mixture was kept at 240°–145°C. for 10 minutes. The mixture was then cooled, and filtered, and the solid residue was washed with petroleum ether (b.p. 40°–60°C.; 750ml.), and crystallised from dimethylsulphoxide to give 2,8-dimethoxycarbonyl-4,6-dihydroxy-10-methylpyrido[3,2-g]quinoline, m.p. 296°C.

EXAMPLE 13

The methods described in Example 12 were repeated using an equivalent amount of 2,6-diamino-1-chlorobenzene in place of 2,6-diamino-1-methylbenzene. There was thus obtained 2,8-dicarboxy-10-chloro-4,6-dihydroxypyrido[3,2-g]quinoline, m.p. above 300°C.

EXAMPLE 14

The methods described in Examples 7 and 8 were repeated using the appropriate phenylenediamine as starting material, and the following compounds were obtained:

2,8-dicarboxy-4,10-dihydroxy-6-n-propoxy-1,7-phenanthroline, m.p. 294°C. (decomposition) (crystallising with one molecule of solvent from dimethylsulphoxide) from 2,4-diamino-1-n-propoxy-benzene;

2,8-dicarboxy-6-ethoxy-4,10-dihydroxy-1,7-phenanthroline, m.p. 286°–287°C. (decomposition) crystallising as a hemihydrate from dimethylsulphoxide) from 2,4-diamino-phenetole:

2,8-dicarboxy-4,10-dihydroxy-6-methoxy-1,7-phenanthroline, m.p. above 320°C. (crystallising with one molecule of solvent from dimethylsulphoxide) from 2,4-diaminoanisole;

2,8-dicarboxy-6-fluoro-4,10-dihydroxy-1,7-phenanthroline, m.p. above 320°C. (crystallised from dimethylsulphoxide) from 2,4-diamino-1-fluorobenzene; and 2,8-dicarboxy-6-n-heptyl-4,10-dihydroxy-1,7-phenanthroline, m.p. 296°C. (decomposition) (crystallised from dimethylsulphoxide, and washed with boiling ethanol) from 2,4-diamino-1-n-heptylbenzene.

The 2,4-diamino-1-n-propoxybenzene used in the preparation of the said 6-n-propoxy derivative was obtained by hydrogenation of 2,4-dinitro-1-n-propoxybenzene, in a similar way to that described in Example 7 for the preparation of 2,4-diamino-1-n-butylbenzene. The 2,4-diamino-1-n-propoxybenzene so obtained had m.p. 84°–86°C. after crystallisation from benzene.

The 2,4-diamino-1-fluorobenzene used in the preparation of the said 6-fluoro derivative was obtained in essentially the same way from 1-fluoro-2,4-dinitrobenzene, and it was an oil (diacetyl derivative, m.p. 189°–191°C., crystallised from water) which was used directly for the subsequent reaction with acetylene dicarboxylic acid dimethyl ester. Likewise, the 2,4-diamino-1-n-heptylbenzene used in the preparation of the said 6-n-heptyl derivative was obtained by hydrogenation of 1-n-heptyl-2,4-dinitrobenzene.

The 2,4-diamino-1-n-heptylbenzene so obtained was used directly for the reaction with acetylene dicarboxylic acid dimethyl ester. The said 1-n-heptyl-2,4-dinitrobenzene was obtained by nitration of n-heptylbenzene in a similar manner to that described for the nitration of n-pentylbenzene in Example 7.

EXAMPLE 15

A solution of 2,8-diethoxycarbonyl-4,10-dihydroxy-6-phenoxy-1,7-phenanthroline monohydrate (0.5g.) in a mixture of hot glacial acetic acid (10ml.) and hydrochloric acid (15ml. of 3N) was heated under reflux for two hours. The mixture was cooled and then filtered, and the solid residue was washed with boiling chloroform. There was thus obtained 2,8-dicarboxy-4,10-dihydroxy-6-phenoxy-1,7-phenanthroline hemihydrate, m.p. 306°–307°C. (decomposition).

The 2,8-diethoxycarbonyl-4,10-dihydroxy-6-phenoxy-1,7-phenanthroline used in the above process was obtained as a monohydrate of m.p. 214°–215°C. (crystallised from ethanol) by a similar method to that described in Example 1, using 2,4-diamino-diphenyl ether as starting material.

EXAMPLE 16

The method described in Example 7 was repeated, but using 1,3-diamino-4-bromobenzene as starting material in place of 2,4-diamino-1-n-butylbenzene, and there was thus obtained 6-bromo-2,8-dimethoxycarbonyl-4,10-dihydroxy-1,7-phenanthroline, m.p. 208°–210°C.

EXAMPLE 17

The method described in Example 15 was repeated, but using 6-bromo-4,10-dihydroxy-2,8-dimethoxycarbonyl-1,7-phenanthroline as starting material and continuing the heating under reflux for 10 hours. There was thus obtained 6-bromo-2,8-dicarboxy-4,10-dihydroxy-1,7-phenanthroline, m.p. 318°–320°C. (decomposition).

EXAMPLE 18

A mixture of 4,10-dihydroxy-2,8-dimethoxycarbonyl-6-piperidino-1,7-phenanthroline (1.4g.) and hydrochloric acid (30ml. of 3N) was stirred and heated under reflux for 6 hours. A clear solution was obtained, and then the product precipitated from the boiling solution. The mixture was cooled and filtered, and the solid residue was washed twice with boiling chloroform. The solid was crystallised from dimethylsulphoxide and there was thus obtained 2,8-dicarboxy-4,10-dihydroxy-6-piperidino-1,7-phenanthroline (crystallising with one molecule of solvent), m.p. 296°C. (decomposition).

The 4,10-dihydroxy-2,8-dimethoxycarbonyl-6-piperidino-1,7-phenanthroline used as starting material was obtained as follows:

A solution of acetylene dicarboxylic acid dimethyl ester (5.2g.) in dry methanol (25ml.) was added to a solution of 2,4-diamino-1-piperidinobenzene (3.3g.) in dry methanol (50ml.) and, when the exothermic reaction was over, the mixture was heated under reflux for 3 hours. The solvent was removed by distillation at 60°C. in vacuo, and the residue of bis-anil (m.p. 122°–124°C., after crystallisation from methanol) was added in portions to boiling diphenyl ether (50ml.), and the mixture heated at 240°–245°C. until no more methanol was liberated (5 minutes). The solution was cooled, and diluted with petroleum ether (b.p. 40°–60°C.; 300ml.). The solvent was decanted from the precipitated solid, and the solid was crystallised from methanol. There was thus obtained 4,10-dihydroxy-2,8-dimethoxycarbonyl-6-piperidino-1,7-phenanthroline, m.p. 268°–270°C.

EXAMPLE 19

The appropriate methods described in Example 18 were repeated using the appropriate phenylenediamine as starting material, and the following compounds were obtained:

2,8-dicarboxy-4,10-dihydroxy-6-morpholino-1,7-phenanthroline, m.p. 317°C. (decomposition) (crystallising with one molecule of solvent from dimethylsulphoxide) from 2,4-diamino-1-morpholinobenzene;

6-di-n-butylamino-2,8-dicarboxy-4,10-dihydroxy-1,7-phenanthroline, m.p. 279°–280°C. (decomposition) from 2,4-diamino-1-di-n-butylaminobenzene;

4,10-dihydroxy-2,8-dimethoxycarbonyl-6-N-methylanilino-1,7-phenanthroline, m.p. 239°–240°C. (decomposition) (crystallised from dioxan), and 2,8-dicarboxy-4,10-dihydroxy-6-N-methylanilino-1,7-phenanthroline, m.p. 304°–306°C. (decomposition) (crystallised from dimethylsulphoxide) from 2,4-diamino-1-N-methylanilinobenzene;

6-diethylamino-4,10-dihydroxy-2,8-dimethoxycarbonyl-1,7-phenanthroline, m.p. 209°–210°C. (crystallised from methanol) from 2,4-diamino-1-diethylaminobenzene; and 2,8-dicarboxy-6-hexahydroazepin-1-yl-4,10-dihydroxy-1,7-phenanthroline, m.p. 292°–293°C. (decomposition) from 2,4-diamino-1-hexahydroazepinylbenzene.

The 2,4-diamino-1-morpholinobenzene used in the above process was obtained as follows:

A suspension of 4-(2,4-dinitrophenyl)morpholine (5g.) in ethanol (125ml.) was shaken with hydrogen at room temperature and atmospheric pressure in the presence of a palladium-on-charcoal catalyst (0.5g. of 5%). When the theoretical amount of hydrogen (2.9 l.) had been absorbed, the mixture was filtered and the filtrate evaporated to dryness under reduced pressure. The residue of 2,4-diamino-1-morpholinobenzene (m.p. 126°–128°C., crystallised from benzene/petroleum ether, b.p. 40°–60°C.) was used directly for the subsequent reaction with acetylene dicarboxylic acid dimethyl ester.

The 2,4-diamino1-di-n-butylaminobenzene, 2,4-diamino-N-methylanilinobenzene and 2,4-diamino-1-hexahydroazepinylbenzene were obtained similarly by hydrogenation of 2,4-dinitro-1-di-n-butylaminobenzene, 2,4-dinitro-N-methyldiphenylamine and 2,4-dinitro-1-hexahydroazepinylbenzene respectively. The products were oils and were used directly for the subsequent reaction with acetylene dicarboxylic acid dimethyl ester.

EXAMPLE 20

A suspension of 2,8-dicarboxy-6-methyl-4,10-dihydroxy-1,7-phenanthroline (1g.) in n-butanol (10ml.) was saturated with hydrogen chloride gas, and then heated under reflux for 2 hours while a stream of hydrogen chloride was passed in. The clear solution was left for 12 hours at room temperature, then filtered, and the crystalline residue washed with dry ether. The solid was dissolved as much as possible in cold chloroform, the mixture filtered, and the filtrate evaporated to dryness under reduced pressure. The solid residue was crystallised from n-butanol, and there was obtained the hydrochloride of 2,8-di-n-butoxycarbonyl-4,10-dihydroxy-6-methyl-1,7-phenanthroline, m.p. 182°–184°C. (decomposition), which re-solidifies above 185°C. and re-melts at 265°C. To obtain the free base, the hydrochloride was stirred and washed with water until acid-free, and the mixture was then filtered and the solid residue crystallised from n-butyl acetate. There was thus obtained 2,8-di-n-butoxycarbonyl-4,10-dihydroxy-6-methyl-1,7-phenanthroline, m.p. 133°–135°C.

EXAMPLE 21

The method described in Example 20 was repeated, but using n-amyl alcohol in place of n-butanol, and there was obtained 4,10-dihydroxy-6-methyl-2,8-di-n-pentyloxycarbonyl-1,7-phenanthroline, m.p. 137°–139°C. (crystallised from diethyl ether).

EXAMPLE 22

The method described in Example 8 was repeated, but using 2,8-diethoxycarbonyl-3,6,9-trimethyl-4,10-dihydroxy-1,7-phenanthroline in place of 6-n-butyl-2,8-dimethoxycarbonyl-4,10-dihydroxy-1,7-phenanthroline, and there was obtained 2,8-dicarboxy-3,6,9-trimethyl-4,10-dihydroxy-1,7-phenanthroline, m.p. above 320°C. (crystallising with one molecule of solvent from dimethylsulphoxide).

The 2,8-diethoxycarbonyl-3,6,9-trimethyl-4,10-dihydroxy-1,7-phenanthroline used in the above process was obtained by the method described in Example 7, but using 2,4-diaminotoluene and ethyl ethoxalylproprionate in place of 2,4-diamino-1-n-butylbenzene and acetylene dicarboxylic acid dimethyl ester respectively. There was thus obtained 2,8-dimethoxycarbonyl-3,6,9-trimethyl-4,10-dihydroxy-1,7-phenanthroline, m.p. 205°–206°C. (crystallised from 2-ethoxyethanol).

EXAMPLE 23

A suspension of 2,8-diethoxycarbonyl-6-methyl-4,10-dihydroxy-1,7-phenanthroline (0.37g.) in ethanol (10ml.) was mixed with a solution of morpholine (0.087g.) in ethanol. The mixture was heated to boiling, and sufficient ethanol (40ml.) was added to obtain almost complete dissolution. The hot mixture was filtered, the filtrate cooled and the resulting crystalline salt filtered off. There was thus obtained the morpholine salt of 2,8-diethoxycarbonyl-6-methyl-4,10-dihydroxy-1,7-phenanthroline, molecular formula $C_{19}H_{18}O_6N_2 \cdot C_4H_9ON$, m.p. 213°–214°C. (decomposition) (crystallised from ethanol).

EXAMPLE 24

The method described in Example 1 was repeated, but using α-chloronaphthalene in place of diphenyl ether as solvent during the cyclisation, and the mixture was heated at 220°–230°C. for 10 minutes. There was thus obtained 2,8-diethoxycarbonyl-4,10-dihydroxy-6-methyl-1,7-phenanthroline, m.p. 208°–209 C. (crystallised from dioxan).

EXAMPLE 25

The method described in Example 1 was repeated except that the diphenyl ether was replaced by polyphosphoric acid. The residue obtained after removing the benzene was added to polyphosphoric acid (50ml.) heated at 125°C., and the mixture was stirred and heated at 130°C. for 15 minutes. The mixture was cooled to 90°C., poured on to ice, filtered, and the filtrate basified with ammonium hydroxide (density 0.88) to pH 4. The aqueous layer was decanted from the precipitated gum, which solidified on rubbing with acetone. The mixture was filtered, and the solid residue crystallised from dioxan. There was thus obtained 2,8-diethoxycarbonyl-4,10-dihydroxy-6-methyl-1,7-phenanthroline, m.p. 208°–209°C.

EXAMPLE 26

The method described in Example 6 was repeated, but using an equivalent amount of 6-n-butyl-2,8-dicarboxy-4,10-dihydroxy-1,7-phenanthroline in place of 2,8-dicarboxy-4,10-dihydroxy-6-methyl-1,7-phenanthroline, and there was obtained the disodium salt of 6-n-butyl-2,8-dicarboxy-4,10-dihydroxy-1,7-phenanthroline as a tetrahydrate after drying at room temperature in air; n.m.r. spectrum (in $D_2O$): $H_3$ (or $H_9$) single peak (6.60 δ); $H_9$ (or $H_3$) single peak (6.70 δ); $H_5$ single peak (7.25 δ); aromatic —$CH_2$ of n—$C_4H_9$ multiplet (2.20 δ). U.V. spectrum in water: λ max 231 A (ε 35,000), 293 A (ε 16,400), 310 A inflection (ε 13,400), 346 A (ε 11,900) and 365 A inflection (ε 9,160). An aqueous solution of the disodium salt has pH 4.4.

In a similar way there was obtained the disodium salt of 6-n-propyl-2,8-dicarboxy-4,10-dihydroxy-1,7-phenanthroline tetrahydrate; n.m.r. spectrum (in $D_2O$): $H_3$ (or $H_9$) single peak (6.60 δ); $H_9$ (or $H_3$) single peak (6.70 δ); $H_5$ single peak (7.20 δ); aromatic —$CH_2$ of n—$C_3H_7$ multiplet (2.20 δ). U.V. spectrum in water: λ max 231 A (ε 37,200), 293 A (ε 17,500), 310 A inflection (ε 14,300), 346 A (ε 12,800) and 365 A inflection (ε 9,530). An aqueous solution of the disodium salt had pH 4.4.

EXAMPLE 27

2,8-Diethoxycarbonyl-6-methyl-4,10-dihydroxy-1,7-phenanthroline (0.36g.) was added to a hot solution of N-methylglucamine (0.2g.) in ethanol (5ml.), and the clear solution was cooled and diluted with diethyl ether. The mixture was filtered, and the solid residue was triturated with acetone, and then filtered. There was thus obtained the N-methylglucamine salt of 2,8-diethoxycarbonyl-6-methyl-4,10-dihydroxy-1,7-phenanthroline as a hemihydrate, molecular formula $C_{19}H_{18}O_6N_2 \cdot C_7H_{17}O_5N \cdot \frac{1}{2}H_2O$, m.p. 85°–90°C.

EXAMPLE 28

2,8-Dicarboxy-6-methyl-4,10-dihydroxy-1,7-phenanthroline (0.4g.) was added to a solution of N-methylglucamine (0.39g.) in water (3ml.) and stirred until the solution had pH 4. The mixture was filtered, and the filtrate was diluted with ethanol (15ml.) and decanted from the precipitated gum. The gum was stirred with acetone, and then filtered. The solid residue was the N-methylglucamine salt of 2,8-dicarboxy-6-methyl-4,10-dihydroxy-1,7-phenanthroline, m.p. 210°C. (decomposition), and had the composition $C_{15}H_{10}O_6N_2 \cdot 2C_7H_{17}O_5N \cdot H_2O$. The aqueous solution in water had pH 4.

EXAMPLE 29

The method described in Example 7 was repeated, but using 1,4-diamino-2-bromobenzene as starting material in place of 2,4-diamino-1-n-butylbenzene, and the intermediate bis-anil (m.p. 100°–101°C. after crystallisation from methanol) was cyclised in diphenyl ether by the method described in the same Example. The produce (m.p. 283°–284°C., crystallised from dimethylsulphoxide) was either 5-bromo-2,7-dimethoxycarbonyl-4,9-dihydroxypyrido[2,3-g]quinoline or 5-bromo-3,8-dimethoxycarbonyl-1,10-dihydroxy-4,7-phenanthroline (believed more likely to be the latter). The product was hydrolysed by heating with a mixture of hydrochloric acid and acetic acid for 10 hours, according to the method described in Example 15. There was thus obtained 5-bromo-2,7-dicarboxy-4,9-dihydroxypyrido[2,3-g]quinoline or 5-bromo-3,8-dicarboxy-1,10-dihydroxy-4,7-phenanthroline (believed more likely to be the latter), m.p. 290°C. (decomposition).

EXAMPLE 30

The method described in Example 7 was repeated, but using 1,4-diamino-2-chlorobenzene as starting material in place of 2,4-diamino-1-n-butylbenzene, and the intermediate bis-anil (m.p. 100°–102°C. after crystallisation from ethanol) was cyclised in diphenyl ether by the method described in the same Example.

The product [m.p. 292°–294°C. (decomposition), crystallised from dimethylsulphoxide] was either 5-chloro-2,7-dimethoxycarbonyl-4,9-dihydroxypyrido[2,3-g]quinoline or 5-chloro-3,8-dimethoxycarbonyl-1,10-dihydroxy-4,7-phenanthroline (believed more likely to be the latter). The product was hydrolysed by heating with sodium hydroxide according to the method described in Example 8. There was thus obtained 5-chloro-2,7-dicarboxy-4,9-dihydroxypyrido[2,3-g]quinoline or 5-chloro-3,8-dicarboxy-1,10-dihydroxy-4,7-phenanthroline (believed more likely to be the latter) as a hemihydrate after washing with boiling ethanol, m.p. 280°C. (decomposition).

EXAMPLE 31

The method described in Example 7 was repeated using 1,4-diamino-2-trifluoromethylbenzene as starting material in place of 2,4-diamino-1-n-butylbenzene, and the intermediate crude bis-anil was cyclised in diphenyl ether by the method described in the same example. The product [m.p. 302°C. (decomposition); crystallised from dimethylsulphoxide] was either 5-trifluoromethyl-2,7-dimethoxycarbonyl-4,9-dihydroxypyrido[2,3-g]quinoline or 5-trifluoromethyl-3,8-dimethoxycarbonyl-1,10-dihydroxy-4,7-phenanthroline (believed more likely to be the latter). The product was hydrolysed by heating with sodium hydroxide as described in Example 2. There was thus obtained 5-trifluoromethyl-2,7-dicarboxy-4,9-dihydroxypyrido[2,3-g]quinoline or 5-trifluoromethyl-3,8-dicarboxy-1,10-dihydroxy-4,7-phenanthroline (believed more likely to be the latter as a dihydrate, m.p. 320°C. (decomposition).

EXAMPLE 32

The disodium salt of 6-n-propyl-2,8-dicarboxy-4,10-dihydroxy-1,7-phenanthroline (20g.; screened through mesh size 90; all mesh sizes herein are according to British Standard 410:1962) and lactose (15g.; screened through mesh size 90) were thoroughly mixed. There was thus obtained a powder formulation suitable for inhalation for medicinal purposes.

EXAMPLE 33

An aerosol formulation was prepared consisting of finely divided disodium salt of 6-n-butyl-2,8-dicarboxy-4,10-dihydroxy-1,7-phenanthroline (2% w/w; screened through mesh size 90), isoprenaline sulphate (0.1% w/w; screened through mesh size 90), and propellant to 100% w/w (the propellant was a 60:40 v/v mixture of dichloro-difluoromethane and 1,2-dichloro-1,1,2,2-tetrafluoroethane). There was thus obtained an aerosol formulation suitable for inhalation for medicinal purposes.

EXAMPLE 34

A mixture of 6-n-butyl-2,8-diethoxycarbonyl-4,10-dihydroxy-1,7-phenanthroline (50g.) and mannitol (25g.) was filled into hard gelatin capsules. There were thus obtained capsules containing between 25mg. and 500mg. of active ingredient which were suitable for oral administration for therapeutic purposes.

The active ingredient used in the above process was replaced by equivalent quantity of 2,8-diethoxycarbonyl-4,10-dihydroxy-6-n-propyl-1,7-phenanthroline, and there were thus obtained capsules containing between 25mg. and 500mg. of active ingredient which were suitable for oral administration for therapeutic purposes.

EXAMPLE 35

2,8-Dimethoxycarbonyl-4,6-dihydroxy-10-phenoxypyrido[3,2-g]quinoline (1g.) was heated with 10% w/v aqueous sodium hydroxide (10ml.) on a steam bath for 15 minutes. The hot solution was acidified with concentrated hydrochloric acid and the resultant precipitate was collected by filtration, and then washed successively with water and acetone. There was thus obtained 2,8-dicarboxy-4,6-dihydroxy-10-phenoxypyrido[3,2-g]quinoline m.p. above 340°C.

The 2,8-dimethoxycarbonyl derivative used as starting material was obtained as follows:

A solution of acetylene dicarboxylic acid dimethyl ester (4.3g.) in dry methanol (10ml.) was added to a solution of 2,6-diaminophenyl phenyl ether (3g.) in dry methanol (15ml.) and, when the exothermic reaction was over, the mixture was heated under reflux for 3 hours. The mixture was cooled and filtered, and the solid residue was crystallised from methyl acetate to give the bis-anil, m.p. 147°–148°C. The bis-anil (3.6g.) was added to boiling diphenyl ether (25ml.), and the mixture was kept at the boiling point until no more methanol was liberated (about 15 minutes). The solution was cooled and diluted with petroleum ether (b.p. 40°–60°C.). The mixture was filtered and the solid residue was washed with more petroleum ether (b.p. 40°–60°C.). The solid residue was crystallised from dimethyl sulphoxide, washed with methanol, and dried. There was thus obtained 2,8-dimethoxycarbonyl-4,6-dihydroxy-10-phenoxypyrido[3,2-g]quinoline, m.p. 272°–273°C.

The 2,6-diaminophenyl phenyl ether used as starting material was obtained as follows:

A suspension of 2,6-dinitrophenyl phenyl ether (6.5g.) in ethanol (100ml.) was shaken with hydrogen at room temperature and atmospheric pressure in the presence of palladium-on-charcoal (0.5g. of 5% w/w) as catalyst. When the theoretical amount of hydrogen (3.4 l.) had been absorbed, the mixture was filtered and the filtrate evaporated to dryness under reduced pressure. The solid residue (4.9g.) was crystallised from cyclohexane to give 2,6-diaminophenyl phenyl ether, m.p. 110°–111°C.

EXAMPLE 36

The method described in Example 35 was repeated using an equivalent amount of 2,8-dimethoxycarbonyl-4,6-dihydroxy-10-ethoxypyrido[3,2-g]quinoline in place of 2,8-dimethoxycarbonyl-4,6-dihydroxy-10-phenoxypyrido[3,2-g]quinoline. There was thus obtained 2,8-dicarboxy-10-ethoxy-4,6-dihydroxypyrido[3,2-g]quinoline, m.p. above 330°C.

The 2,8-dimethoxycarbonyl derivative used as starting material was prepared from acetylene dicarboxylic acid dimethyl ester as described in Example 35, but using an equivalent quantity of 2-ethoxy-1,3-diaminobenzene in place of the 2,6-diaminophenyl phenyl ether. The bis-anil so obtained (m.p. 119°–120°C. after crystallisation from methanol) was added to boiling diphenyl ether and kept at boiling point until no more methanol was liberated (about 10 minutes). The reaction-product was worked up as described in Example 35 in respect of 2,8-dimethoxycarbonyl-4,6-dihydroxy-10-phenoxypyrido[3,2-g]quinoline. There was thus obtained 2,8-dimethoxycarbonyl-4,6-dihydroxy-10-ethoxypyrido[3,2-g]quinoline, m.p. 247°–248°C. (crystallised from pyridine).

The 2-ethoxy-1,3-diaminobenzene used as starting material was obtained by hydrogenation of 2-ethoxy-1,3-dinitrobenzene in a manner similar to that described in Example 35 for the preparation of 2,6-diaminophenyl phenyl ether. The 2-ethoxy-1,3-diaminobenzene so obtained was an oil which was used directly for the reaction with acetylene dicarboxylic acid dimethyl ester.

EXAMPLE 37

The appropriate methods described in Examples 35 and 36 were repeated using 2-n-propoxy-1,3-diaminobenzene as starting material, and there was thus obtained 2,8-dicarboxy-4,6-dihydroxy-10-n-propoxypyrido[3,2-g]quinoline, m.p. above 330°C.

The 2-n-propoxy-1,3-diaminobenzene used as starting material was obtained by hydrogenation of 2-n-propoxy-1,3-dinitrobenzene in a manner similar to that described in Example 35 for the preparation of 2,6-diaminophenyl phenyl ether. The 2-n-propoxy-1,3-diaminobenzene so obtained was an ol which was used directly for the reaction with acetylene dicarboxylic dimethyl ester to give the bis-anil, m.p. 119°–120°C. (crystallised from methanol), which was cyclised by heating in diphenyl ether to give 2,8-dimethoxycarbonyl-4,6-dihydroxy-10-n-propoxypyrido[3,2-g]quinoline, m.p. 245°–247°C. (crystallised from acetic acid).

EXAMPLE 38

The method described in Example 35 was repeated using 2,8-dimethoxycarbonyl-4,6-dihydroxy-10-phenylpyrido[3,2-g]quinoline as starting material, and there was thus obtained 2,8-dicarboxy-4,6-dihydroxy-10-phenylpyrido[3,2-g]quinoline, m.p. above 340°C.

The dimethoxycarbonyl derivative used as starting material was obtained from acetylene dicarboxylic acid dimethyl ester and 2,6-diaminodiphenyl in a manner similar to that described in Example 35 for the preparation of 2,8-dimethoxycarbonyl-4,6-dihydroxy-10-phenoxypyrido[3,2-g]quinoline. The intermediate bis-anil, m.p. 155°–156°C. (crystallised from methyl acetate), was cyclised by heating in diphenyl ether to give 2,8-dimethoxycarbonyl-4,6-dihydroxy-10-phenylpyrido[3,2-g]quinoline, m.p. 325°–326°C. (with decomposition) (crystallised from acetic acid).

EXAMPLE 39

A solution of acetylene dicarboxylic acid dimethyl ester (4.2g.) in dry methanol (10ml.) was added to a solution of 3,5-diamino-4-ethoxytoluene (2.4g.) in dry methanol (10ml.) and, when the initial exothermic reaction was over, the mixture was stirred at room temperature for one hour. The mixture was filtered and the solid residue was crystallised from methanol to give the bis-anil, m.p. 94°–96°C. The bis-anil (3g.) was added to boiling diphenyl ether (15ml.), and the mixture kept at the boiling point until no more methanol was liberated (about 10 minutes). The solution was cooled and filtered, and the solid residue crystallised from glacial acetic acid. There was thus obtained 2,8-dimethoxycarbonyl-10-ethoxy-4,6-dihydroxy-5-methylpyrido[3,2-g]quinoline, m.p. 250°–251°C.

The 3,5-diamino-4-ethoxytoluene used as starting material was obtained, as an oil, by hydrogenation of 4-ethoxy-3,5-dinitrotoluene in a manner similar to that described in Example 35 for the preparation of 2,6-diaminophenyl phenyl ether.

EXAMPLE 40

The method described in Example 35 was repeated, but using 2,8-dimethoxycarbonyl-10-ethoxy-4,6-dihydroxy-5-methylpyrido[3,2-g]quinoline as starting material. There was thus obtained 2,8-dicarboxy-10-ethoxy-4,6-dihydroxy-5-methylpyrido[3,2-g]quinoline, m.p. 324°C. (decomposition) (crystallised from dimethylsulphoxide).

EXAMPLE 41

A mixture of 2,8-diethoxycarbonyl-4,6-dihydroxy-10-morpholinopyrido[3,2-g]quinoline (0.8g.), glacial acetic acid (10ml.) and hydrochloric acid (10ml. of 20%) was stirred and heated under reflux for 6 hours. A clear solution was obtained, and then the product precipitated from the boiling solution. The mixture was filtered hot, and the solid residue was washed successively with water (20ml.), acetone (20ml.) and ether (20ml.). There was thus obtained 2,8-dicarboxy-4,6-dihydroxy-10-morpholinopyrido[3,2-g]quinoline, m.p. above 350°C.

The 2,8-diethoxycarbonyl derivative used as starting material was prepared as follows:

A solution of acetylene dicarboxylic acid diethyl ester (4.1g.) in dry ethanol (10ml.) was added to a solution of 2,6-diamino-1-morpholinobenzene (2.3g.) in dry ethanol (10ml.) and, when the initial exothermic reaction was over, the mixture was stirred at room temperature for 3 hours. The solvent was removed by distillation under reduced pressure, and the residue triturated with ether (10ml.) and then filtered. The solid residue was crystallised from ethanol to give the bis-anil, m.p. 143°–144°C. This bis-anil (3.2g.) was added to boiling diphenyl ether (20ml.), and the mixture was kept at the boiling point until no more ethanol was liberated (about 5 minutes). The solution was cooled and filtered, and the solid residue was crystallised from glacial acetic acid. There was thus obtained 2,8-diethoxycarbonyl-4,6-dihydroxy-10-morpholinopyrido[3,2-g]quinoline, m.p. 327°–328°C.

The 2,6-diamino-1-morpholinobenzene (m.p. 163°–165°C., crystallised from toluene) used as starting material was obtained by hydrogenation of 2,6-dinitro-1-morpholinobenzene in a manner similar to that described in Example 35 for the preparation of 2,6-diaminophenyl phenyl ether.

The 2,6-dinitro-1-morpholinobenzene itself was obtained as follows:

A mixture of 1-chloro-2,6-dinitrobenzene (6g.), morpholine (6g.) and ethanol (25ml.) was heated under reflux on a steam bath for 20 hours. The mixture was poured into cold water, the mixture filtered, and the solid residue crystallised from ethanol. There was thus obtained 2,6-dinitro-1-morpolinobenzene, m.p. 112°–114°C.

EXAMAPLE 42

The appropriate methods described in Example 41 were repeated using 2,6-diamino-1-diethylaminobenzene as starting material, and there was thus obtained 2,8-dicarboxy-10-diethylamino-4,6-dihydroxypyrido[3,2-g]quinoline, m.p. above 350°C.

The 2,6-diamino-1-diethylaminobenzene used as starting material was obtained by hydrogenation of 1-diethylamino-2,6-dinitrobenzene in a manner similar to that described in Example 35 for the preparation of 2,6-diaminophenylphenyl ether. The 2,6-diamino-1-diethylaminobenzene was an oil which was used directly for the reaction with acetylene dicarboxylic acid diethyl ester to give the bis-anil (an oil), which was cyclised by heating in diphenyl ether, as described in Example 41, to give 2,8-diethoxycarbonyl-10-diethylamino-4,6-dihydroxypyrido[3,2-g]-quinoline, m.p. 267°–268°C. (crystallised from dioxan).

The 1-diethylamino-2,6-dinitrobenzene was obtained as follows:

A mixture of 1-chloro-2,6-dinitrobenzene (6g.), diethylamine (6.2g.) and ethanol (25ml.) was heated under reflux on a steam bath for 2 hours. The mixture was poured into water, filtered, and the solid residue crystllised from ethanol. There was thus obtained 1-diethylamino-2,6-dinitrobenzene, m.p. 46°–47°C.

EXAMPLE 43

The appropriate methods described in Example 41 were repeated using 2,6-diamino-1-hexahydroazepinylbenzene as starting material, and there was thus obtained 2,8-dicarboxy -10-hexahydroazepin-1-yl-4,6-dihydroxyprido[3,2g]quinoline, m.p. 326°–328°C. (decomposition).

The 2,6-diamino-1-hexahydroazepinylbenzene used as starting material was obtained by hydrogenation of 1-hexahydroazepinyl-2,6-dinitrobenzene in a manner similar to that described in Example 35 for the preparation of 2,6-diaminophenyl phenyl ether. The 2,6-diamino-hexahydroazepinylbenzene so obtained was an oil which was used directly for the reaction with acetylene dicarboxylic diethyl ester to give the bis-anil (an oil), which was cyclised by heating in diphenyl ether, as described in Example 41, to give 2,8-diethoxycarbonyl-10-hexahydroazepin-1-yl-4,6-dihydroxypyrido[3,2-g]quinoline, m.p. 301°–302°C. (crystallised from dioxan).

The 1-hexahydroazepinyl-2,6-dinitrobenzene was obtained as follows:

A mixture of 1-chloro-2,6-dinitrobenzene (6g.), hexamethyleneimine (7g.) and ethanol (25ml.) was heated under reflux on a steam bath for 9 hours. The mixture was poured into water and filtered, and the solid residue was dissolved in ether, the solution dried over magnesium sulphate, filtered and the solvent evaporated. The residue was crystallised from petroleum ether (b.p. 40°–60°C.) and there was thus obtained 1-hexahydroazepinyl-2,6-dinitrobenzene, m.p. 69°–70°C.

EXAMPLE 44

A solution of acetylene dicarboxylic acid diethyl ester (6.8g.) in dry ethanol (15ml.) was added to a solution of 2,6-diamino-N-methyl-diphenylamine (4.3g.) in dry ethanol (20ml.) and, when the initial exothermic reaction was over, the mixture was stirred at room temperature for 12 hours. The solvent was removed by distillation under reduced pressure and the residue dissolved in ether (200ml.). The ether solution was washed successively with N-hydrochloric acid (50ml.), 2N-sodium hydroxide (50ml.) and water, and then dried over magnesium sulphate. The mixture was filtered, the filtrate evaporated, and the residual oil added to boiling diphenyl ether (15ml.). The mixture was kept at the boiling point until or more ethanol was liberated (about 5 minutes). The solution was cooled and filtered, the solid residue washed successively with ether (30ml.) and acetone (20ml.), and then crystallised from dioxan. There was thus obtain 2,8-diethoxycarbonyl-4,6-dihydroxy-10-N-methylanilinopyrido[3,2g]quinoline, m.p. 230°–232°C.

The 2,6-diamino-N-methyldipenylamine used as starting material was obtained by hydrogenation of N-methyl-2,6-dinitrodiphenylamine in a manner similar to that described in Example 35 for the preparation of 2,6-diaminophenyl phenyl ether.

The N-methyl-2,6-dinitrodiphenylamine itself was obtained as follows:

2,6Dinitrodiphenylamine (5g.) was added slowly in portions to a stirred suspension of sodium hydride (0.5g. of an 80% dispersion) in dry dimethylformamide (50ml.), and, after stirring for 15 minutes, methyl iodide (2ml.) was added. The mixture was stirred at room temperature for 2 hours and then poured into water (200ml.). The mixture was extracted with ether, the ether extract washed with water, dried over magnesium sulphate, filtered and the filtrate evaporated. The solid residue was crystallised from ethanol and there was thus obtained N-methyl-2,6-dinitrodiphenylamine as deep red platelets, m.p. 96°–97°C.

EXAMPLE 45

The method described in Example 41 was repeated, but using 2,8-diethoxycarbonyl-4,6-dihydroxy-10-N-methyl-anilinopyrido[3,2quinoline as starting material. There was thus obtained 2,8-dicarboxy-4,6-dihydroxy-10-N-methylanilinopyrido[3,2-g]quinoline, m.p. above 340°C.

EXAMPLE 46

2,8-Dicarboxy-10-ethoxy-4,6-dihydroxy-5-methyl-pyrido[3,2-g]quinoline (0.7g.) was stirred with a solution of sodium hydrogen carbonate (0.4g.) in water (8ml.) for 10 minutes. The mixture was filtered, the filtrate diluted with ethanol (8ml.), and the resulting mixture filtered. The solid residue was successively washed with ethanol (10ml.) and ether (10ml.), and then dried. There was thus obtained the disodium salt of 2,8-dicarboxy-10-ethoxy-4,6-dihydroxy-5-methyl-pyrido[3,2-g]quinoline; n.m.r. spectrum (in $D_2O$): $H_3$ and $H_7$ singlet 2H ($\delta$ 6.38); 5-methyl, singlet 3H ($\delta$ 2.69); $CH_3$ of ethoxy, triplet 3H ($\delta$ 1.38); $CH_2$ of ethoxy, quartet 2H ($\delta$ 3.70).

EXAMPLE 47

An aerosol formulation was prepared consisting of finely divided disodium salt of 2,8-dicarboxy-10-ethoxy-4,6-dihydroxy-5-methylpyrido[3,2-g]quinoline (2% w/w; screened through mesh size 90), isoprenaline sulphate (0.1% w/w; screened through mesh size 90), and propellant to 100% w/w (the propellant was a 60:40 v/v mixture of dichloro-difluoromethane and 1,2-dichloro-1,1,2,2-tetrafluoroethane). There was thus obtained an aerosol formulation suitable for inhalation formedicinal purposes.

What I claim is:

1. As a pharmaceutical composition of matter for the treatment of a syndrome or disease initiated by an antigen-antibody reaction:

A. a functionally-effective amount of a compound selected from the group consisting of pyridoquinoline derivatives of the formula:

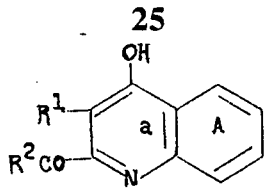

wherein
benzene ring A is a member selected from the group consisting of chemical groups of the formulae:

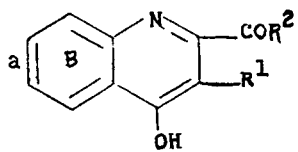

and

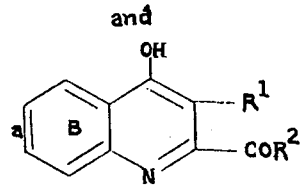

$a$ in the formulae III and V indicates the common bond between the pyridine ring and the benzene ring A in the formula I; $R^1$ is hydrogen; and $R^2$ is a member selected from the group consisting of hydroxy, $C_{1-6}$ alkoxy, $C_{7-10}$ phenylalkoxy and phenoxy, and benzene ring B is a member selected from the group consisting of (a) benzene, and (b) benzene bearing not more than two substituents selected from the group consisting of $C_{1-8}$ alkyl, cycloalkyl of not more than 6 carbon atoms, $C_{1-6}$ alkoxy, trifluoromethyl, phenyl, phenoxy, halogen and —$NR^3R^4$ and —NZ wherein $R^3$ stands for $C_{1-6}$ alkyl, $R^4$ is a member selected from the group consisting of $C_{1-6}$ alkyl and phenyl, and —NZ stands for a heterocyclic radical selected from N-piperidino, N-morpholino and hexahydroazepin-1-yl; and non-toxic pharmaceutically-acceptable salts thereof; and (B) an inert non-toxic pharmaceutically-acceptable diluent or carrier.

2. A method for the treatment of a syndrome or disease initiated by an antigen-antibody reaction in a hoist in need of said treatment, which comprises administering to said host a functionally-effective amount of a composition as defined in claim 1.

3. A method as claimed in claim 2 for the treatment of asthma, hay fever, urticaria or an auto-immune disease.

* * * * *

UNITED STATES PATENT OFFICE
CERTIFICATE OF CORRECTION

Patent No. 3,984,551　　　　　　　　Dated October 5, 1976

Inventor(s) Wilson Shaw WARING

It is certified that error appears in the above-identified patent and that said Letters Patent are hereby corrected as shown below:

In item [30],

Foreign Application Priority Data should read:

Oct. 5, 1970    United Kingdom.......47151/70
   Nov. 18, 1970   United Kingdom.......54868/70
   Feb. 22, 1971   United Kingdom.......5096/71
   Apr. 16, 1973   United Kingdom.......18188/73

Col. 2, line 13, "formmulae" should read --formulae--

Col. 2, line 30, a comma (,) should be inserted after "alkyl"

Col. 5, line 22, "which is one" should read --which in one--

Col. 6, line 34, "proces" should read --process--

Col. 7, lines 3-4, "pharmaceutcial" should read --pharmaceutical--

Col. 7, line 35, "wherein in a formulae II to V" should read
　　　　　　　　　--wherein a in formulae II to V--

Col. 7, lines 55-56, "pharmaceutically" is misspelled

Col. 13, line 59, "240°-145°C." should read --240°-245°C.--

Col. 16, line 30, "2,4-diaminol-..." should read
　　　　　　　　　--2,4-diamino-1-... --

Col. 17, lines 14-15, "...proprionate" should read --propionate--

Col. 17, line 41, "209 C" should read --209°C--

UNITED STATES PATENT OFFICE
CERTIFICATE OF CORRECTION

Patent No. 3,984,551                    Dated      October 5, 1976

Inventor(s) Wilson Shaw WARING

It is certified that error appears in the above-identified patent and that said Letters Patent are hereby corrected as shown below:

Col. 19, line 36, "the latter as" should read --the latter) as--

Col. 21, line 26, "ol" should read --oil--

Col. 21, last line, "methylpvrido..." should read --methylpyrido--

Col. 23, line 27, "dihydroxyprido" should read --dihydroxypyrido--

Col. 24, line 1, "until or more" should read --until no more--

Col. 24, line 15, "2,6Dinitro..." should read --2,6-Dinitro...--

Col. 24, line 31, "methyl-anilinopyrido[3,2 quinoline" should read --methylanilinopyrido[3,2-g]quinoline--

Col. 26, line 23, "hoist" should read --host--

Signed and Sealed this twelfth Day of July 1977

[SEAL]

Attest:

RUTH C. MASON
*Attesting Officer*

C. MARSHALL DANN
*Commissioner of Patents and Trademarks*